(12) United States Patent
Reunamaki et al.

(10) Patent No.: US 11,026,579 B2
(45) Date of Patent: Jun. 8, 2021

(54) CONTROLLING DERIVATION OF A BIOMETRIC CHARACTERISTIC OF A SUBJECT

(71) Applicant: Nokia Technologies Oy, Espoo (FI)

(72) Inventors: Jukka Reunamaki, Tampere (FI); Arto Palin, Viiala (FI)

(73) Assignee: Nokia Technologies Oy, Espoo (FI)

( * ) Notice: Subject to any disclaimer, the term of this patent is extended or adjusted under 35 U.S.C. 154(b) by 186 days.

(21) Appl. No.: 16/094,987

(22) PCT Filed: Apr. 22, 2016

(86) PCT No.: PCT/FI2016/050264
§ 371 (c)(1),
(2) Date: Oct. 19, 2018

(87) PCT Pub. No.: WO2017/182693
PCT Pub. Date: Oct. 26, 2017

(65) Prior Publication Data
US 2019/0125188 A1 May 2, 2019

(51) Int. Cl.
*A61B 5/00* (2006.01)
*H04B 17/318* (2015.01)
(Continued)

(52) U.S. Cl.
CPC .......... *A61B 5/0024* (2013.01); *A61B 5/0022* (2013.01); *A61B 5/0205* (2013.01); *A61B 5/1117* (2013.01); *G16H 10/60* (2018.01); *G16H 40/63* (2018.01); *G16H 40/67* (2018.01); *H04B 17/318* (2015.01); *H04L 67/12* (2013.01); *H04W 4/38* (2018.02); *H04W 8/005* (2013.01);
(Continued)

(58) Field of Classification Search
CPC ... A61B 5/0024; A61B 5/0022; A61B 5/0205; A61B 5/117; A61B 5/01; A61B 5/02125; A61B 5/024; A61B 5/0402; A61B 5/0476; A61B 5/0488; H04B 17/318; G16H 40/67; G16H 10/60; G16H 40/63; H04W 4/38; H04W 8/005; H04W 84/12; H04L 67/12
USPC .......................................................... 600/301
See application file for complete search history.

(56) References Cited

U.S. PATENT DOCUMENTS

| 8,693,452 B1 | 4/2014 | Lauff et al. ................... 370/338 |
| 2007/0156626 A1* | 7/2007 | Roehm .................... A61B 5/02 600/300 |

(Continued)

*Primary Examiner* — Erin M Piateski
(74) *Attorney, Agent, or Firm* — Harrington & Smith

(57) ABSTRACT

According to an example embodiment, there is provided a method in a device including a sensor portion for deriving, on basis of one or more sensor signals that are descriptive of respective characteristics of a body of a living subject, at least a first biometric signal that is descriptive of a first biometric characteristic of said subject, the method including detecting presence of another device that is capable of providing, over a wireless link, information carried in a second biometric signal that is descriptive of a second biometric characteristic of the same subject, receiving, from the detected device via the wireless link, one or more values of the second biometric characteristic carried in said second biometric signal and selectively enabling or disabling derivation of said first biometric signal in dependence of said one or more values of the second biometric characteristic received from said detected device.

20 Claims, 6 Drawing Sheets

200

Detect presence of a device that is capable of generating a second biometric signal that is descriptive of a certain biometric characteristic of a human subject of interest
210

Receive information carried in the second biometric signal from the detected device via the wireless link
220

Selectively enable or disable derivation of a first biometric signal that is descriptive of the same biometric cahracteristic of the same human subject in dependence of the information received from the detected device
230

(51) Int. Cl.
| | |
|---|---|
| *H04L 29/08* | (2006.01) |
| *H04W 8/00* | (2009.01) |
| *H04W 4/38* | (2018.01) |
| *A61B 5/11* | (2006.01) |
| *A61B 5/0205* | (2006.01) |
| *G16H 10/60* | (2018.01) |
| *G16H 40/63* | (2018.01) |
| *G16H 40/67* | (2018.01) |
| *A61B 5/01* | (2006.01) |
| *A61B 5/024* | (2006.01) |
| *A61B 5/021* | (2006.01) |
| *A61B 5/318* | (2021.01) |
| *A61B 5/369* | (2021.01) |
| *A61B 5/389* | (2021.01) |
| *H04W 84/12* | (2009.01) |

(52) U.S. Cl.
CPC ............... *A61B 5/01* (2013.01); *A61B 5/024* (2013.01); *A61B 5/02125* (2013.01); *A61B 5/318* (2021.01); *A61B 5/369* (2021.01); *A61B 5/389* (2021.01); *H04W 84/12* (2013.01)

(56) References Cited

U.S. PATENT DOCUMENTS

| | | | |
|---|---|---|---|
| 2008/0119749 A1 | 5/2008 | Haro et al. | 600/528 |
| 2009/0069642 A1 | 3/2009 | Gao et al. | 600/300 |
| 2011/0221590 A1 | 9/2011 | Baker et al. | 340/539.12 |
| 2012/0003933 A1 | 1/2012 | Baker et al. | 455/41.2 |
| 2013/0225200 A1* | 8/2013 | Ben Hamida | H04W 64/00 455/456.1 |
| 2013/0274565 A1* | 10/2013 | Langer | A61B 5/02438 600/301 |
| 2013/0317753 A1* | 11/2013 | Kamen | G16H 40/20 702/19 |
| 2014/0275928 A1 | 9/2014 | Acquista et al. | 600/382 |
| 2016/0269999 A1* | 9/2016 | Hwang | H04W 4/80 |

* cited by examiner

200

Detect presence of a device that is capable of generating a second biometric signal that is descriptive of a certain biometric characteristic of a human subject of interest

210

Receive information carried in the second biometric signal from the detected device via the wireless link

220

Selectively enable or disable derivation of a first biometric signal that is descriptive of the same biometric cahracteristic of the same human subject in dependence of the information received from the detected device

```
┌─────────────────────────────────────────┐
│ Carry out device discovery procedure to │
│         detect presence of a device     │
│                                         │
│                  212                    │
└─────────────────────────────────────────┘
                    │
                    ▼
┌─────────────────────────────────────────┐
│ Carry out service discovery procedure   │
│ with the detected device to detect      │
│ availability of information that is     │
│ descriptive of the certain biometric    │
│ characteristic therein                  │
│                                         │
│                  214                    │
└─────────────────────────────────────────┘
                    │
                    ▼
┌─────────────────────────────────────────┐
│ Verify that the information descriptive │
│ of the certain biometric characteristic │
│ available in the detected device is     │
│ descriptive of the certain biometric    │
│ characteristic of the same human        │
│ subject as the first biometric signal   │
│                                         │
│                  216                    │
└─────────────────────────────────────────┘
```

Figure 6

US 11,026,579 B2

CONTROLLING DERIVATION OF A BIOMETRIC CHARACTERISTIC OF A SUBJECT

This patent application is a U.S. National Stage application of International Patent Application Number PCT/FI2016/050264 filed Apr. 22, 2016, which is hereby incorporated by reference in its entirety.

TECHNICAL FIELD

The example and non-limiting embodiments of the present invention relate to extracting one or more biometric characteristics pertaining to a living subject in a power-efficient manner.

BACKGROUND

Recent developments in sensory technologies that enable measurement of various biometric characteristics of a person or an animal have enabled, together with advances on wireless communication technologies, healthcare solutions for personal use where a monitoring device is arranged to monitor at least one biometric characteristic of the person and to transfer the obtained biometric data to a database stored in a remote server via a wireless link to enable remote tracking of the biometric data and/or subsequent analysis of biometric data e.g. for medical purposes. Herein, we refer to such a monitoring device as a mobile biometric monitoring device or as a biometric gateway (GW) device.

Examples of biometric characteristics monitored by a mobile biometric monitoring device include vital signs such as body temperature, heart rate, respiratory rate, blood pressure and oxygen saturation level. Further examples of such biometric characteristics include signals that are descriptive of a condition or aspect of human physiology, such as signal(s) descriptive one of the following: electrocardiogram (ECG), phonocardiogram (PCG), electroencephalogram (EEG), blood volume pulse (BVP), electromyogram (EMG).

While mobile (and non-mobile) biometric monitoring devices have traditionally found use as part of medical treatment in professional domain e.g. in a hospital environment, mobile biometric monitoring devices are becoming increasingly popular in monitoring of biometric characteristics of people also outside the professional medical domain. Typical examples of such semi-professional or non-professional use include monitoring of one or more biometric characteristics of a person who suffers from a long-term medical condition or one or more biometric characteristics of an elderly person in general in home environment, monitoring of one or more biometric characteristics of a person who is working in a hazardous environment, monitoring of one or more biometric characteristics of an athlete under excessive physical stress, etc.

A mobile biometric monitoring device necessarily relies on a power supply that is provided as part of the device or that is otherwise carried together with the mobile biometric monitoring device by a person whose biometric characteristics are being monitored using the device. Typically, the power supply comprises a battery installed in or connected to the mobile biometric monitoring device. In many use cases, especially those that fall outside the typically well-controlled professional medical domain, energy-efficient operation of the mobile biometric monitoring device plays an important role in ensuring reliable operation and convenient use of the biometric monitoring device via avoidance of frequent replacement/recharging of the power supply and/or even complete drainage of the power supply.

SUMMARY

According to an example embodiment, there is provided a method in a device comprising a sensor portion for deriving, on basis of one or more sensor signals that are descriptive of respective characteristics of a body of a living subject, at least a first biometric signal that is descriptive of a first biometric characteristic of said subject, the method comprising detecting presence of another device that is capable of providing, over a wireless link, information carried in a second biometric signal that is descriptive of a second biometric characteristic of the same subject, receiving, from the detected device via the wireless link, one or more values of the second biometric characteristic carried in said second biometric signal and selectively enabling or disabling derivation of said first biometric signal in dependence of said one or more values of the second biometric characteristic received from said detected device.

According to another example embodiment, a device is provided, the device comprising a sensor portion for deriving, on basis of one or more first sensor signals that are descriptive of respective characteristics of a body of a living subject, at least a first biometric signal that is descriptive of a first biometric characteristic of said subject, a communication apparatus for wireless communication over a wireless link, and a control portion arranged to cause the device to perform at least the following: detect presence of another device that is capable of providing, over the wireless link, information carried in a second biometric signal that is descriptive of a second biometric characteristic of the same subject, receive, from the detected device via the wireless link, one or more values of the second biometric characteristic carried in said second biometric signal, and selectively enable or disable derivation of said first biometric signal in dependence of said one or more values of the second biometric characteristic received from said detected device.

According to another example embodiment, a device is provided, the device comprising a sensor means for deriving, on basis of one or more sensor signals that are descriptive of respective characteristics of a body of a living subject, at least a first biometric signal that is descriptive of a first biometric characteristic of said subject, a communication means for wireless communication over a wireless link, and a control means for causing the device to perform at least the following: detect presence of another device that is capable of providing, over the wireless link, information carried in a second biometric signal that is descriptive of a second biometric characteristic of the same subject, receive, from the detected device via the wireless link, one or more values of the second biometric characteristic carried in said second biometric signal, and selectively enable or disable derivation of said first biometric signal in dependence of said one or more values of the second biometric characteristic received from said detected device.

According to another example embodiment, a computer program is provided, the computer program comprising computer readable program code configured to cause performing at least the method according to the example embodiment described in the foregoing when said program code is executed on a computing apparatus:

The computer program according to an example embodiment may be embodied on a volatile or a non-volatile computer-readable record medium, for example as a computer program product comprising at least one computer readable non-transitory medium having program code stored thereon, the program which when executed by an apparatus cause the apparatus at least to perform the operations described hereinbefore for the computer program according to an example embodiment of the invention.

The exemplifying embodiments of the invention presented in this patent application are not to be interpreted to pose limitations to the applicability of the appended claims. The verb "to comprise" and its derivatives are used in this patent application as an open limitation that does not exclude the existence of also unrecited features. The features described hereinafter are mutually freely combinable unless explicitly stated otherwise.

Some features of the invention are set forth in the appended claims. Aspects of the invention, however, both as to its construction and its method of operation, together with additional objects and advantages thereof, will be best understood from the following description of some example embodiments when read in connection with the accompanying drawings.

BRIEF DESCRIPTION OF FIGURES

The embodiments of the invention are illustrated by way of example, and not by way of limitation, in the figures of the accompanying drawings, where FIG. 1 schematically illustrates some components of a wireless communication arrangement according to an example embodiment;

FIG. 4 illustrates a method according to an example embodiment;

FIG. 6 illustrates a method according to an example embodiment; and

DESCRIPTION OF SOME EMBODIMENTS

Figure 1:
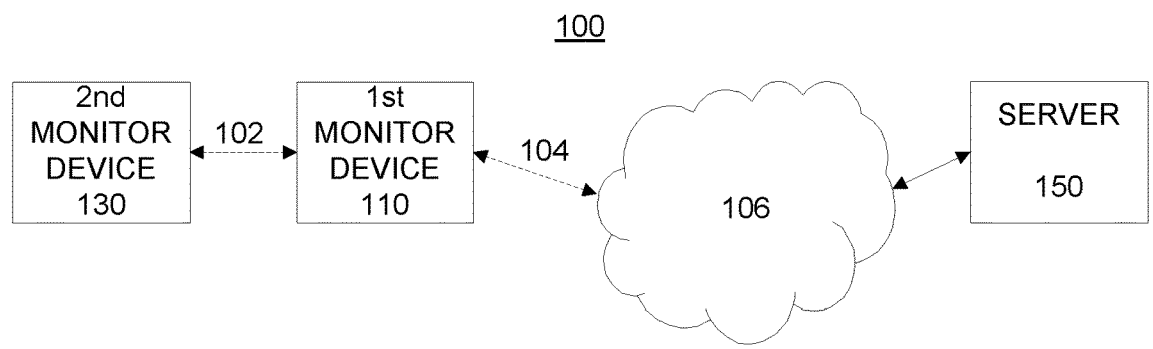

FIG. 1 schematically illustrates a block diagram of some components and/or entities of a wireless communication arrangement 100 to depict an exemplifying framework for one or more embodiments of the present invention. The wireless communication arrangement 100 comprises a primary monitoring device 110 for monitoring at least one biometric characteristic of a human subject, a secondary monitoring device 130 for monitoring at least one biometric characteristic of a human subject and a server device 150 for storing and/or processing information descriptive of one or more biometric characteristics. The primary monitoring device 110 is connectable to a network 106 via a wireless link 104, which network 106 enables a connection further to the server device 150. The primary monitoring device 110 is further connectable to the secondary monitoring device 130 via a wireless link 102.

Each of the primary and secondary monitoring devices 110, 130 are typically respective special purpose devices capable of deriving respective at least one biometric characteristic of a human subject for transfer to another device or entity for subsequent analysis or viewing and/or for presentation via a user interface (UI) to one or more users, e.g. to the subject himself/herself and/or to one or more other people (e.g. medical personnel).

In particular, the primary monitoring device 110 may employ (a first set of) one or more sensors to capture respective sensor signals that are descriptive of respective characteristics of a body of a human subject and to generate, on basis of the captured sensor signals, one or more biometric signals that are descriptive of respective one or more biometric characteristics of the human subject for transfer to the server device 150, whereas the secondary biometric monitoring device 130 may employ (a second set of) one or more sensors to capture respective sensor signals that are descriptive of respective characteristics of the body of the same human subject and to generate, on basis of the captured sensor signals, one or more biometric signals that are descriptive of respective one or more biometric characteristic of the same human subject for transfer to the primary biometric monitoring device 110 and/or for presentation via a UI of the secondary biometric monitoring device 130 to a user.

The examples described in the foregoing and in the following refer to capturing sensor signals that are descriptive of a respective characteristic of a human body and to deriving biometric signals that are descriptive of a respective biometric characteristic of a human subject. This, however, is a non-limiting example and these examples generalize into for capturing sensor signals that are descriptive of a respective characteristic of a body of a living being or subject and into deriving biometric signals that are descriptive of a respective biometric characteristic of the living being/subject, which living being/subject may be e.g. a human subject or an animal.

The examples described in the foregoing and in the following refer to a biometric signal that is descriptive of a certain biometric characteristic of a human subject in singular. This, however, is a choice made in favor of editorial clarity of the description, and in other examples the biometric signal may consist of two or more distinct signals (e.g. sub-signals) that are jointly descriptive of the certain biometric characteristic of the human subject.

Figure 2:
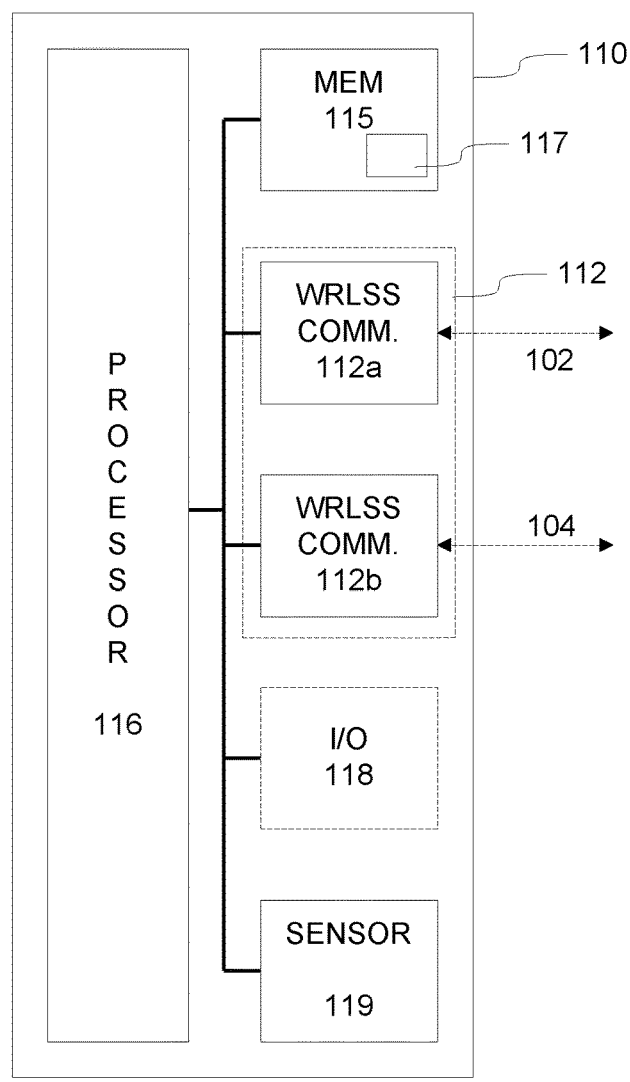
FIG. 2 schematically illustrates some components of a monitoring device according to an example embodiment.

FIG. 2 depicts a block diagram of some components of an exemplifying primary monitoring device 110. The primary monitoring device 110 may comprise further components or portions in addition to those depicted in FIG. 2. In this regard, the primary monitoring device 110 further comprises e.g. a power supply for providing electrical power to components of the primary monitoring device 110. The power supply may comprise, e.g. a rechargeable or non-rechargeable battery, which battery may be replaceable or it may be installed in the primary monitoring device 110 in a fixed manner.

The primary monitoring device 110 is typically provided as a mobile device that is frequently or even constantly carried by its user. As an example in this regard, the primary monitoring device 110 is a mobile device that a user may carry with him/her as he/she chooses. In another example, the primary monitoring device 110 is a wearable device that the user is able to wear through wearing an installation arrangement designed for the purpose. In a further example, the primary monitoring device 110 is an implantable device that can be partially or even fully implanted to a body of the user.

The primary monitoring device 110 comprises a communication portion 112. The communication portion 112 comprises at least a first communication apparatus 112a for wireless communication with other apparatuses and it may further comprise a second communication apparatus 112b for wireless communication with other apparatuses. The communication portion 112 may comprise one or more further communication apparatuses for wireless and/or wired communication with other apparatuses. The first communication apparatus 112a may enable, for example, wireless communication with other devices by using a wireless communication technique or protocol that enables a point-to-point or a point-to-multipoint wireless connection with another device. The first communication apparatus 112a may be employed to establish the wireless link 102 that enables wireless communication with the secondary monitoring device 130. The second communication apparatus 112b, if included in the primary monitoring device 110, may apply communication technique/protocol different from that of the first communication apparatus 112a and it may enable establishing the wireless link 104 to the network 106, which in turn enables communication with the server device 150.

The primary monitoring device 110 further comprises a processor 116 and a memory 115 for storing data and computer program code 117. The primary monitoring device 110 may further comprise user I/O (input/output) components 118 that may be arranged, possibly together with the processor 116 and a portion of the computer program code 117, to provide a user interface (UI) for receiving input from a user of the primary monitoring device 110 and/or providing output to the user of the primary monitoring device 110. The user I/O components 118 may comprise hardware components such as a display, a touchscreen, a touchpad, a mouse, a keyboard, and/or an arrangement of one or more keys or buttons, etc. The processor 116 may be arranged to control operation of the primary monitoring device 110 e.g. in accordance with a portion of the computer program code 117 stored in the memory 115 and possibly further in accordance with the user input received via the user I/O components 118 and/or in accordance with information received via the communication portion 112. The memory 115 and a portion of the computer program code 117 stored therein may be further arranged to, with the processor 116, to provide a control portion or a control function for controlling operation of a communication apparatus of the communication portion 112, possibly together with a control portion or a control function that may be provided within the respective communication apparatus of the communication portion 112 (which will be described later in this text). These control functions may be, separately or jointly, referred to as control means (of the primary monitoring device 110).

The primary monitoring device 110 further comprises a sensor portion 119 for deriving one or more biometric signals that are descriptive of a respective biometric characteristic of the human subject on basis of one or more sensor signals. The sensor portion 119 may include one or more sensors for capturing respective sensor signals that are descriptive of respective characteristics of a body of a human subject. In a straightforward example, a sensor signal, i.e. a signal captured by a respective one of the one or more sensors, is provided as such as the respective biometric signal. In another example the sensor portion comprises an analysis portion (not shown in FIG. 2) for generating, on basis of the captured sensor signal(s), one or more biometric signals that are descriptive of a respective biometric characteristic of the human subject. The control means may operate the sensor portion 119 and the analysis portion (if present) to obtain the one or more biometric signals as desired and operate the communication portion 112 (e.g. the second communication apparatus 112b) to transfer at least part of the information carried in the one or more biometric signals to the server device 150 for subsequent analysis and/or viewing. Herein, the analysis portion serves as a logical entity that may be provided, instead of being provided as part of the sensor portion 119, for example, as part of the control means or as an entity separate from the sensor portion 119 and the control means. Due to its operation as a device that (both captures and) delivers the biometric signals pertaining to the human subject to the server device 150, the primary monitoring device 110 may also be referred to as biometric gateway device.

Figure 3:
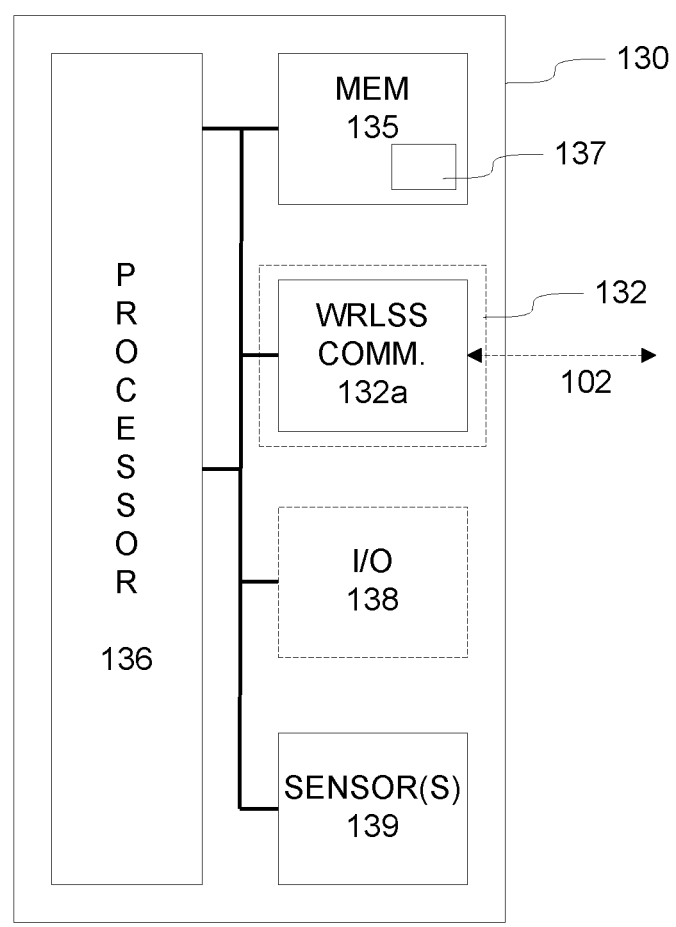
FIG. 3 schematically illustrates some components of a monitoring device according to an example embodiment.

FIG. 3 depicts a block diagram of some components of an exemplifying secondary monitoring device 130. The secondary monitoring device 130 may comprise further components or portions in addition to those depicted in FIG. 3. As an example in this regard, the secondary monitoring device 130 further comprises e.g. a power supply for providing electrical power to components of the secondary monitoring device 130. The power supply may comprise, e.g. a rechargeable or non-rechargeable battery, which battery may be replaceable or it may be installed in the secondary monitoring device 130 in a fixed manner.

The secondary monitoring device 130 is typically provided as a mobile device that is frequently carried by its user. As an example in this regard, the primary monitoring device 110 is a mobile device that a user may carry with him/her or wear as he/she chooses. An example of such a device is an activity tracker that may be provided e.g. as a wrist band, as a smart watch or as a wireless sensor arrangement wearable by the human subject by using a specially designed fitting arrangement such as a chest band.

The secondary monitoring device 130 comprises a communication portion 132. The communication portion 132 comprises at least a communication apparatus 132a for wireless communication with other apparatuses. The communication apparatus 132a may enable, for example, wireless communication with other devices by using a wireless communication technique or protocol that enables a point-to-point or a point-to-multipoint wireless connection with another device, in particular with the communication apparatus 112a. The communication apparatus 132a may hence be employed to establish the wireless link 102 that enables the secondary monitoring device 130 to wirelessly communicate with the primary monitoring device 110.

The secondary monitoring device 130 further comprises a processor 136 and a memory 135 for storing data and computer program code 137. The secondary monitoring device 130 may further comprise user I/O (input/output) components 138 that may be arranged, together with the processor 136 and a portion of the computer program code 137, to provide a user interface (UI) for receiving input from a user of the secondary monitoring device 130 and/or providing output to the user of the secondary monitoring device 130. The user I/O components 138 may comprise hardware components such as a display, a touchscreen, a touchpad, a mouse, a keyboard and/or an arrangement of one or more keys or buttons, etc. The processor 136 may be arranged to control operation of the secondary monitoring device 130 in accordance with a portion of the computer program code 137 stored in the memory 135 and possibly further in accordance with the user input received via the user I/O components 138 and/or in accordance with information received via the communication portion 132. The memory 135 and a portion of the computer program code 137 stored therein may be further arranged, with the processor 136, to provide a control portion or a control function for controlling operation of a communication apparatus of the communication portion 132, possibly together with a control portion or a control function that may be provided within the respective communication apparatus of the communication portion 132 (which will be described later in this text). These control functions may be, separately or jointly, referred to as control means (of the secondary monitoring device 130).

The secondary monitoring device 130 further comprises a sensor portion 139 for deriving one or more biometric signals that are descriptive of a respective biometric characteristic of the human subject on basis of one or more sensor signals. The sensor portion 119 may include one or more sensors for capturing respective sensor signals that are descriptive of respective characteristics of a body of a human subject. In an example, a sensor signal, i.e. a signal captured by a respective one of the one or more sensors, is provided as such as the respective biometric signal. In another example the sensor portion comprises an analysis portion (not shown in FIG. 3) for generating, on basis of the captured sensor signal(s), one or more biometric signals that are descriptive of a respective biometric characteristic of the human subject. The control means may operate the sensor portion 139 and the analysis portion (if present) to derive the one or more biometric signals as desired and operate the communication portion 132 (e.g. the communication apparatus 132a) to transfer at least part of the information carried in the one or more biometric signals to the primary monitoring device 110 for analysis therein and/or for forwarding from the primary monitoring device 110 to the server device 150 for subsequent analysis and/or viewing. In variations of this example, the operation of the analysis portion is provided as part of the control means, or the analysis portion is provided as an entity separate from the sensor portion 139 and the control means.

The server device 150 is typically a remote server device that is arranged to provide a server function that is accessible by a number of primary monitoring devices 110. Although described herein, for editorial clarity of description, as a single entity, the server function described herein by using the server device 150 as an example may be jointly provided by a number of server devices that are arranged to provide a cloud service or a cloud server arrangement.

As described in the foregoing, the communication portions 112 and 132 may comprise, respectively, communication apparatuses 112a and 132a for wireless communication, while the communication portion 112 may further comprise e.g. the communication apparatus 112b for wireless communication. Each of the communication apparatuses 112a, 112b and 132a described in the foregoing may also be referred to as a respective (wireless) communication means. A communication apparatus may be provided e.g. as a respective chipset and/or as a respective communication module. For clarity and brevity of description, each of the communication apparatuses 112a, 112b and 132a may be considered as a respective single logical entity that may also be capable of processing at least some of the information received via the wireless link 102 and/or at least some of the information that is to be transmitted via the wireless link 102 without external control from other components of the respective monitoring device 110, 130 (e.g. from the processor 116, 136, respectively). In an embodiment, a communication apparatus 112a, 112b, 132a comprises e.g. a respective wireless transceiver portion for wireless communication and a respective control portion (or a control function) for controlling operation of the respective wireless transceiver portion and for processing information received/transmitted via the respective wireless transceiver portion. Such a control function may be provided by hardware means, by software means or by a combination of hardware means and software means. As an example in this regard, the communication apparatus 112a, 112b, 132a may comprise a memory, a processor and a portion of a computer program code stored in the memory may be arranged to, with the processor, provide the control function for controlling operation of the respective wireless communication apparatus 112a, 112b, 132a, either independently or jointly with the control function provided by the respective memory 115, 135, a portion of the respective computer program 117, 137 and the respective processor 116, 136 of the respective monitoring device 110, 130.

The wireless link 102 between the first communication apparatus 112a of the communication portion 112 and the communication apparatus 132a of the communication portion 132 (and hence between the primary and secondary monitoring devices 110 and 130) may be provided by employing a suitable short-range wireless communication technique or protocol. Such a wireless link may also be referred to as a local wireless link. The term short-range wireless communication as used herein refers to a wireless communication technique or protocol that enables typical operating range in the scale of tens of meters, e.g. up to 100 meters. However, especially in an indoor environment, the operating range of such short-range wireless communication technique/protocol may be significantly shorter e.g. due to walls and other stationary structures as well as furniture etc. that are likely to partially block or interfere with the radio communication between communication apparatuses 112a, 132a. On the other hand, in favorable conditions in outdoor use the operating range may extend to several hundreds of meters.

Examples of such a wireless technique/protocol include the Bluetooth Basic Rate/Enhanced Data Rate (BT BR/EDR) protocol and the Bluetooth Low Energy (BLE) protocol, both specified e.g. in the Bluetooth Specification Version 4.1, Covered Core Package version: 4.1 (publication date 3 Dec. 2013), incorporated herein by reference in its entirety. In the following, this document is referred to as a Bluetooth Specification. However, the BT BR/EDR and BLE technologies serve as illustrative and non-limiting examples in this regard, and the description generalizes into any short-range wireless communication technique/protocol. A further example of a suitable short-range wireless communication technique/protocol includes Wireless Local Area Network (WLAN) technology specified e.g. in IEEE 802.11 specifications (where the acronym IEEE stands for the Institute of Electrical and Electronics Engineers). Yet further examples of other suitable short-range wireless communication techniques/protocols known in the art include ANT wireless sensor network technology, IEEE 802.15.4 network technology for low-rate wireless personal networks (LR-WPANs), Ultra-Wide Band (UWB) radio technology.

The second wireless communication apparatus 112b in the communication portion 112 of the primary monitoring device 110, if included therein, may be arranged to employ any suitable wireless access technology known in the art to establish the wireless link 104 that enables a connection to the network 106 that further connects the primary monitoring device 110 to the server device 150. As an example in this regard, assuming that the first wireless communication apparatus 112b applies some other communication protocol/technique (such as BT BR/EDR or BLE), the wireless communication apparatus 112b may be arranged to employ the WLAN technology referred to in the foregoing to establish the wireless link 104 with a wireless access point in its vicinity, which wireless link 104 enables the primary monitoring device 110 to access the network 106 that further enables connection to the server device 150. As another example, the wireless communication apparatus 112*b* may be arranged to employ a cellular access technology known in the art to establish the wireless link 104 with a base station of a cellular network, which wireless link 104 enables the primary monitoring device 110 to access the network 106 that further enables connection to the server device 150.

For clarity of description, in the following examples reference is made, in singular, to first and second biometric signals that each are descriptive of a certain (predefined) biometric characteristic of interest, where the first biometric signal is derivable in the primary monitoring device 110 (using first sensor signals obtainable from the sensor portion 119) and the second biometric signal is derivable in the secondary monitoring device 130 (using second sensor signals obtainable from the sensor portion 139). This certain (predefined) biometric characteristic pertains to a human subject and it may comprise e.g. a vital sign of the human subject, such as body temperature, heart rate, respiratory rate, blood pressure or oxygen saturation level. In other examples, the certain (predefined) biometric characteristic may comprise a biosignal, such as ECG, PCG, EEG, BVP, EMG, etc. Although described herein with references to the certain biometric characteristic in singular, it examples readily generalize into a scenario where respective first and second biometric signals are generated for a plurality of (different) biometric characteristics of interest.

Figure 5:
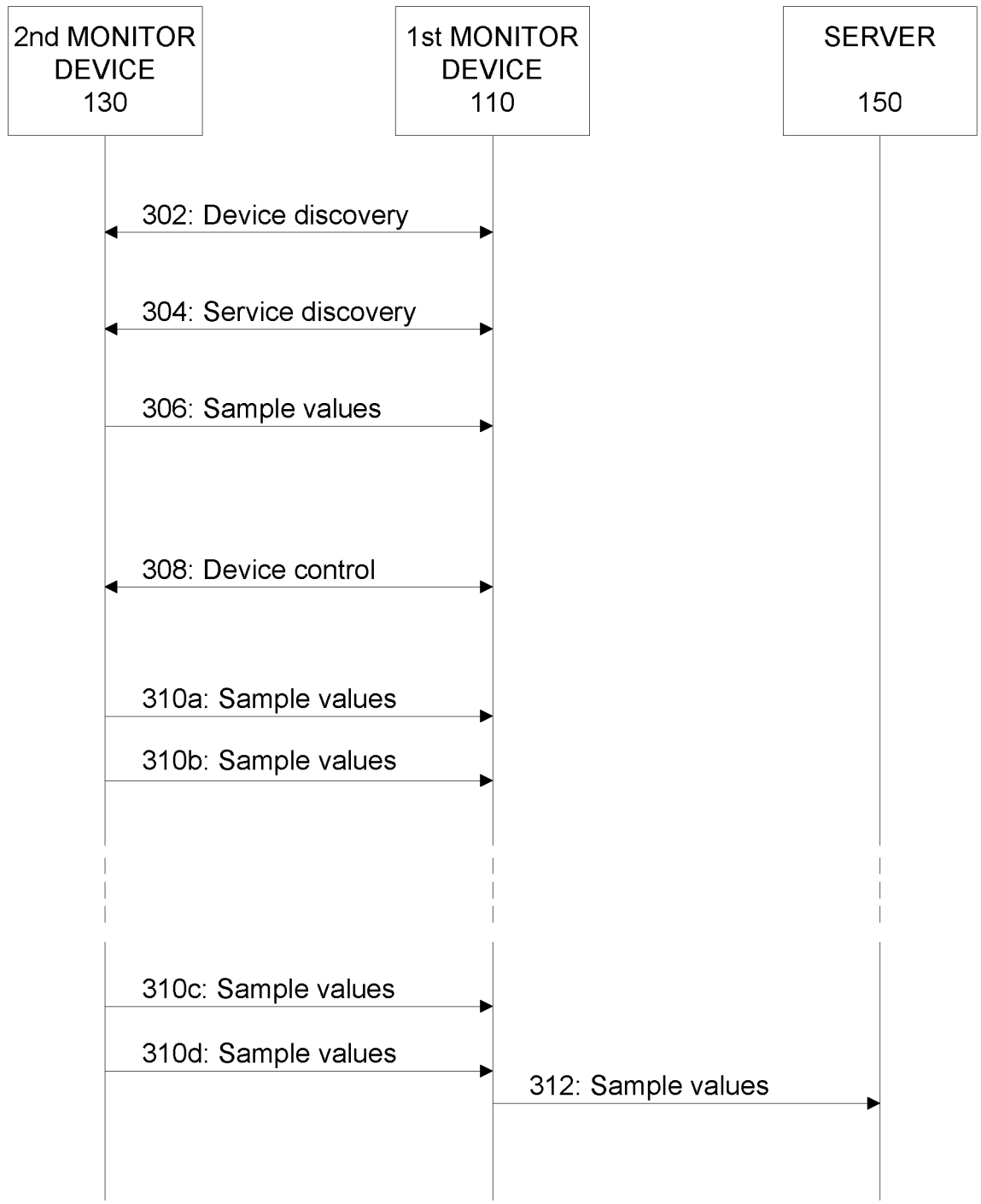
FIG. 5 depicts signaling between elements of the wireless communication arrangement according to an example embodiment.

FIG. 4 illustrates an exemplifying method 200 that may be carried out by the primary monitoring device 110 within the framework of the wireless communication arrangement 100. FIG. 5 depicts a signaling chart that serves to illustrate a non-limiting example of information exchange between the primary monitoring device 110 and the secondary monitoring device 130 as well as between the primary monitoring device 110 and the server device 150 in context of the method 200. FIGS. 4 and 5 provide a non-limiting example that serves to provide a description of some aspects of the present invention.

As a starting point for the method 200 and the signaling depicted in FIG. 5, the control means in the primary monitoring device 110 may operate the sensor portion 119 to capture one or more first sensor signals and operate the analysis portion to process these captured sensor signals into a first biometric signal for transfer of at least part of the information carried therein to the server device 150, where the first biometric signal is descriptive of the certain biometric characteristic of a given human subject. In an example, the first biometric signal is indicative of the value of the certain biometric characteristic as a function of time. In parallel, the control means in the secondary monitoring device 130 may operate the sensor portion 139 to capture one or more second sensor signals and operate the analysis portion to process these captured sensor signals into a second biometric signal, where the second biometric signal is also descriptive of the certain biometric characteristic the given human subject, and where at least part of the information carried in the second biometric signal is available for wireless transfer to other devices over the wireless link 102. In an example, the second biometric signal is indicative of the value of the certain biometric characteristic as a function of time.

The method 200 commences by the primary monitoring device 110 detecting presence of the secondary monitoring device 130, i.e. presence of a device that is capable of generating the second biometric signal that is descriptive of the certain biometric characteristic of the same human subject, as indicated in block 210.

Having detected the secondary monitoring device 130 as one that is capable of providing the primary monitoring device 110 with the second biometric signal that is descriptive of the certain biometric characteristic of the same human subject, the primary monitoring device 110 may start receiving information carried in the second biometric signal from the secondary monitoring device 130 via the wireless link 102, as indicated in block 220.

In the following, we refer to the information received in the primary monitoring device 110 from the secondary monitoring device 130 as secondary biometric information. The secondary biometric information may comprise, for example, a sequence of sample values transmitted from the secondary monitoring device 130, where each sample value indicates the respective value of the second biometric signal. The sample values of the secondary biometric information hence constitute a time series of values that represents the evolution of the certain biometric characteristic over time. The secondary monitoring device 130 may transmit the sample values in a plurality of messages, which plurality of messages may constitute to a sequence (or time series) of messages. Each message may carry one or more (temporally consecutive) sample values of the sequence of sample values.

While in receipt of information carried in the second biometric signal from the secondary monitoring device 130, the primary monitoring device 110 selectively enables or disables derivation of the first biometric signal therein in dependence of the secondary biometric information received from the secondary monitoring device 130, as indicated in block 230.

Referring back to the block 210, FIG. 6 illustrates a method that may be carried out operation(s) pertaining thereto according to an example. Herein, the primary monitoring device 110 may carry out a device discovery procedure to detect another device of desired characteristics, as indicated in block 212 and represented by step 302 in FIG. 5. In the course of the device discovery procedure, the primary monitoring device 110 scans for device discovery messages transmitted from other devices within an operating range of the wireless communication device 112*a*, while the secondary monitoring device 130 transmits device discovery messages to indicate its presence. The device discovery messages may carry, for example, respective indications of identity of the secondary monitoring device 130 and/or services available therein. As an example in this regard, the device discovery advertising messages may comprise BLE advertising messages. The BLE serves, however, as a non-limiting example and other wireless communication techniques/protocols known in the art may be applied instead.

Once the primary monitoring device 110 has detected presence of another device, which in this example is assumed to be the secondary monitoring device 130, the method may continue with service discovery procedure in order to detect availability of a relevant service or information in the secondary monitoring device 130, represented by step 304 in FIG. 5. In particular, the service discovery procedure may be carried out to detect availability of information that is descriptive of the certain biometric characteristic in the secondary monitoring device 130, as indicated in block 214. Depending on the applied wireless communication technique/protocol, the wireless connection between the first and second monitoring devices 110, 130 may be established prior to the service discovery procedure (to enable the service discovery) or the wireless connection between the first and second monitoring devices 110, 130 may be established after the service discovery procedure (in response to detecting availability of information that is descriptive of the certain biometric characteristic being available in the secondary monitoring device 130).

As a further step in the course of the method, successful service detection may be followed by the primary monitoring device 110 verifying that the secondary biometric information originating from the secondary monitoring device 130 is descriptive of the certain biometric characteristic of the same human subject as the first biometric signal derived in the primary monitoring device 110, as indicated in block 216. This may involve the primary monitoring device 110 receiving one or more sample values from the secondary monitoring device 130 (step 306) for comparison with the (temporally) corresponding values carried in the first biometric signal, e.g. according to an outline described in the following:

- requesting and) receiving the secondary biometric information from the secondary monitoring device 130 via the wireless link 102, where the secondary biometric information comprises a sequence of sample values (as described in the foregoing);
- comparing one or more sample values of the received sample values (or values derived therefrom) to temporally corresponding values indicated in (or derived from) the first biometric signal, and
- considering the secondary biometric information to pertain to the same human subject in response to the comparison indicating a difference that is smaller than a predefined margin.

In a variation of the above example, the primary monitoring device 110 may relay the secondary biometric information to the server device 150 (via the wireless link 104) together with information carried in the first biometric signal (i.e. primary biometric information), and the evaluation step(s) to determine whether the secondary biometric information pertains to the same human subject as the primary biometric information are carried out by the server device 150, which subsequently returns an indication of the outcome of the evaluation to the primary monitoring device 110.

Consequently, in response finding the secondary biometric information to pertain to the same human subject as the information carried in the first biometric signal, the primary monitoring device 110 may consider the detection operation of the block 210 as successful and it may continue receiving the secondary biometric information from the secondary monitoring device 130. In contrast, in response to not finding the secondary biometric information to pertain to the same human subject as the information carried in the first biometric signal, the primary monitoring device 110 may consider the detection operation of the block 210 as unsuccessful and it may discontinue receiving the secondary biometric information from the secondary monitoring device 130.

Figure 7:
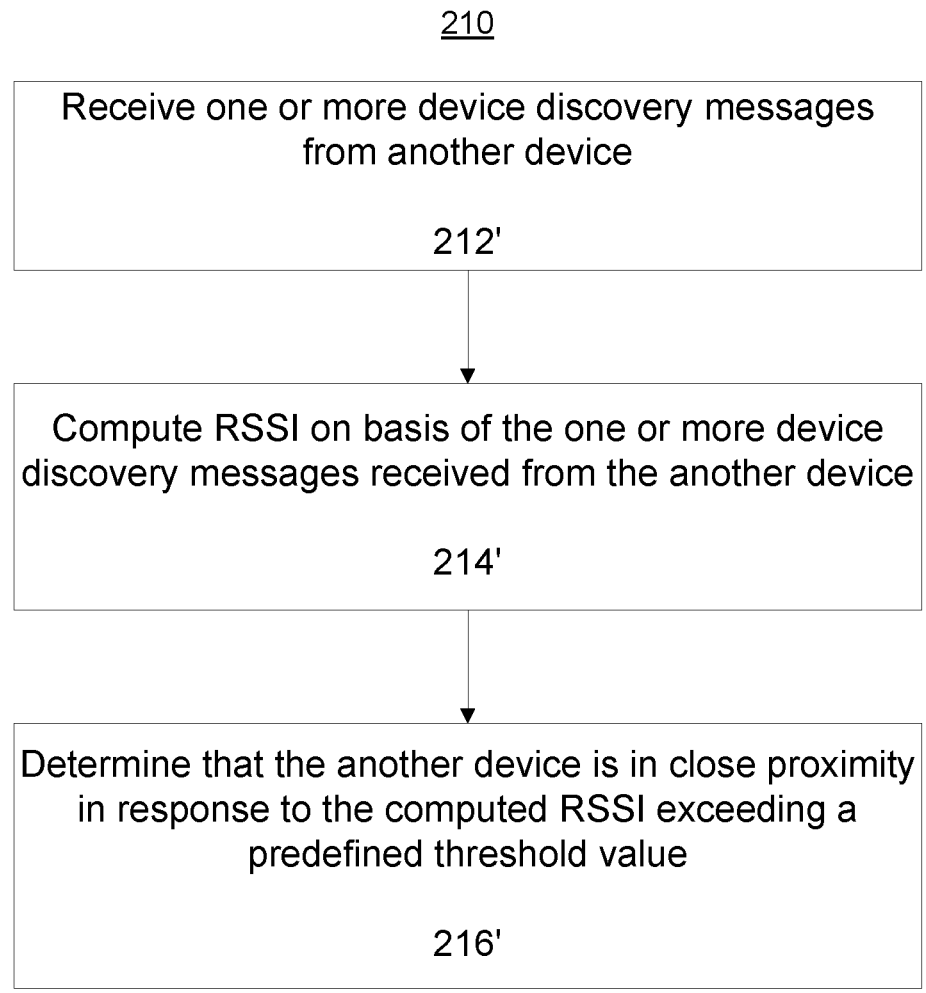
FIG. 7 illustrates a method according to an example embodiment.

In another example, the primary monitoring device 110 may be arranged to consider a wireless device brought into close proximity thereof to be the secondary monitoring device 130 that is capable of generating the second biometric signal that is descriptive of the certain biometric characteristics of the human subject of interest, i.e. the same human subject to which the first biometric signal derived in the primary monitoring device 110 pertains. As an example in this regard, FIG. 7 illustrates a method that may be carried out during operation(s) pertaining to the block 210 of the method 200 according to an example: the primary monitoring device 110 is arranged to receive one or more device discovery messages from another device (block 212'), to compute a received signal strength indication (RSSI) on basis of the one or more device discovery messages originating from the other device (block 214') and to consider the other device to be in close proximity in response to the computed RSSI exceeding a predefined threshold value (block 216'). Consequently, in response to finding the other device to be in close proximity, the primary monitoring device 110 considers the detected device to be the secondary monitoring device 130 and it proceeds to establish the wireless connection thereto and further proceeds into receiving the secondary biometric information therefrom (block 220 of the method 200). With suitable setting of the threshold value for the RSSI the close proximity corresponds or substantially corresponds to the primary and secondary monitoring devices 110, 130 being brought into physical contact with each other in order to trigger the connection establishment therebetween. Such an approach may be referred to as touch-to-select (T2S) operation.

Once the presence of the secondary monitoring device 130 has been detected, the transfer of the secondary biometric information from the secondary monitoring device 130 to the primary monitoring device 110 is initiated or continued (depending on the manner of detecting the presence of the secondary monitoring device 130), as indicated by steps 310a to 310d in FIG. 5.

In general, when in receipt of the secondary biometric information from the secondary monitoring device 130, the control means in the primary monitoring device 110 may disable derivation of the first biometric signal therein when the biometric information received from the secondary monitoring device 130 indicates a normal condition of the human subject, whereas derivation of the first biometric signal may be enabled or re-enabled when the secondary biometric information received from the secondary monitoring device 130 indicates an abnormal condition of the human subject.

Hence, the operation of the primary monitoring device 110 may involve disabling derivation of the first biometric signal therein after having detected presence of the secondary monitoring device 130 and having started reception of the secondary biometric information (e.g. upon step 310a), keeping the derivation of the first biometric signal disabled as long as the secondary biometric information indicates a normal condition of the human subject (e.g. until step 310d), and re-enabling the derivation of the first biometric signal when the secondary biometric information changes to indicate an abnormal condition of the human subject after a period of having indicated a normal condition of the human subject (e.g. after step 310d).

Additionally, the control means in the primary monitoring device 110 may be arranged to re-enable the derivation of the first biometric signal therein after the derivation of the first biometric signal has been continuously disable for at least a predefined time period regardless of the secondary biometric information indicating a normal or abnormal condition of the human subject.

The evaluation whether the secondary biometric information received from the secondary monitoring device 130 indicates a normal condition or an abnormal condition of the human subject may rely on one or more predefined criteria. As an example in this regard, the primary monitoring device 110 may store (e.g. in the memory 115) an indication of the one or more predefined criteria that define normal values associated with the certain biometric characteristic to facilitate selective enabling or disabling of derivation of the first biometric signal in the primary monitoring device 110. Hence, sample values received from the secondary monitoring device 130 meeting the one or more predefined criteria is considered as an indication of a normal condition of the human subject, whereas sample values received from the secondary monitoring device 130 failing to meet one or more of the predefined criteria serves as an indication of an abnormal and potentially unhealthy condition of the human subject. To give concrete (but non-limiting) examples, the one or more criteria may include e.g. one or more of the following requirements:

- a sample value or a value derived from a plurality of sample values must exceed a predefined threshold value;
- a sample value or a value derived from a plurality of sample values must not exceed a predefined threshold value;
- a sample value or a value derived from a plurality of sample values must be within/outside a predefined range of values;
- a sample value or a value derived from a plurality of sample values must match or substantially match one of one or more predefined values;

In the above examples, a value derived from a plurality of sample values may comprise, for example, a value derived as one of the following: a minimum of all sample values within the time period, a maximum of all sample values within the time period, a median of all sample values within the time period, an average of all sample values within the time period, a difference between a maximum and minimum of all sample values within the time period, a difference between the last and first sample values within the time period, etc.

The selective enabling or disabling may hence involve evaluating whether the biometric information received from the secondary monitoring device 130 meets the one or more predefined criteria and

- disabling derivation of the first biometric signal in the primary monitoring device 110 in response the biometric information received from the secondary monitoring device 130 meeting the one or more predefined criteria, or
- enabling derivation of the first biometric signal in the primary monitoring device 110 in response the biometric information received from the secondary monitoring device 130 failing to meet the one or more predefined criteria.

The evaluation whether the biometric information received from the secondary monitoring device 130 meets the one or more predefined criteria may be carried out, for example, on basis of sample values received as the secondary biometric information from the secondary monitoring device 130. Alternatively or additionally, similar evaluation may be carried out on basis of the primary biometric information, e.g. the sample values extracted from the first biometric signal, if it is currently available in the primary monitoring device 110.

The primary monitoring device 110 disabling derivation of the first biometric signal may involve the control means therein controlling the analysis portion to disable generation of the first biometric signal from the available sensor signal(s) in order to avoid unnecessarily investing processing power for generation of the first biometric signal while in receipt of the secondary biometric information, thereby reducing power consumption of the primary monitoring device 110.

Additionally, disablement of derivation of the first biometric signal may further involve the control means in the primary monitoring device 110 controlling the sensor portion 119 to disable generation of the sensors signal(s) employed in derivation of the first biometric signal. This serves to provide further reduction in power consumption in the primary monitoring device 110 via disabling operation of the sensor(s) that serve to capture sensors signal(s) required for derivation of the first biometric signal in the analysis portion.

The primary monitoring device 110 may be further arranged to transmit one or more indications concerning the certain biometric characteristic to the server device 150 via the wireless link 104. In an example, the primary monitoring device 110 continuously (e.g. at predefined intervals) transmits an indication that indicates the current status of the human subject, e.g. whether the most recently obtained biometric information suggests the normal condition or the abnormal condition of the human subject. In another example, such indication is transmitted only in response to the biometric information suggesting abnormal condition of the human subject. The biometric information used as basis for the one or more indications may comprise the primary biometric information and/or the secondary biometric information.

Instead of directly indicating the normal/abnormal condition, the primary monitoring device 110 may transmit one or more indications transferred to the server device 150 may comprise the sample values that constitute the biometric information to the server device 150 for storage and subsequent analysis or viewing therein. Also in this approach, the indications may be transmitted continuously (e.g. at predefined intervals) or in response to the sample values suggesting abnormal condition of the human subject, and the biometric information used as basis for the one or more indications may comprise the primary biometric information and/or the secondary biometric information. As an example in this regard, step 312 of FIG. 5 exemplifies a scenario where sample values of the (primary and/or secondary) biometric information are transmitted to the server device 150 in response to sample values of the secondary biometric information have changed to indicate abnormal condition of the human subject.

In an example, the server device 150 carries out the analysis with respect to biometric information indicating a normal condition or an abnormal condition of the human subject on basis of the sample values received from the primary monitoring device 110. In such an approach, the server device 150 may (store in a memory or a mass storage device provided therein and) carry out evaluation the one or more predefined criteria described in the foregoing. Consequently, if the outcome of the evaluation suggests an abnormal condition of the human subject, the server device 150 may transmit a command or request to the primary monitoring device 110 to instruct enablement or re-enablement of derivation of the first biometric signal.

In an example, after having detected the secondary monitoring device 130 as a device that is capable of providing the primary monitoring device 110 with the secondary biometric information that is descriptive of the certain biometric characteristic of the human subject of interest and having established the wireless connection to the secondary monitoring device 130, the primary monitoring device 110 may further configure or adjust operation of the secondary monitoring device 130 with respect to quality or accuracy of the secondary biometric information transmitted therefrom and/or with respect to format of the information transmitted therefrom, as indicated in step 308 of FIG. 5.

As an example in this regard, the primary monitoring device 110 may be arranged to adjust or control one or more characteristics of the analysis portion of the secondary monitoring device 130 with respect to generation of the second biometric signal therein the secondary monitoring device 130 and/or adjust or control one or more characteristics of the wireless communication apparatus 132*a* in the secondary monitoring device 130 with respect to transmission of messages that carry the secondary biometric information (e.g. the sample values). The control may be provided by the primary monitoring device 110 transmitting one or more commands or requests to the secondary monitoring device 130 via the wireless link 102, while the secondary monitoring device 130 may respond to the commands/requests with respective responses (e.g. to indicate confirmation or refusal the request). As non-limiting examples in this regard, such commands or request transmitted from the primary monitoring device 110 may comprise one or more of the following:

- a request for the analysis means in the secondary monitoring device 130 to provide sample values at an indicated sampling rate (i.e. to provide sample values at an indicated temporal spacing),
- a request for the analysis means in the secondary monitoring device 130 to provide sample values at an indicated resolution (e.g. using an indicated number of bits),
- a request for the wireless communication apparatus 132*a* in the secondary monitoring device 130 to include an indicated number of consecutive sample values in each message transmitted therefrom,
- a request for the wireless communication apparatus 132*a* in the secondary monitoring device 130 to transmit messages including one or more consecutive sample values at an indicated rate.

The commands or requests, as well as possible responses, may be transmitted via the wireless link 102 using a communication protocol designed for this purpose. In another example, a predefined communication framework may be applied for transmitting the commands/requests from the primary monitoring device 110 and for transmitting possible responses from the secondary monitoring device 130. An example of such communication framework is the Generic Attribute Profile (GATT) that may be useable for this purpose in a scenario where BLE is applied to provide the wireless link 102 between the primary and secondary monitoring devices 110, 130.

While the description in the foregoing refers to derivation of the first biometric signal in the primary monitoring device 110 and to derivation of the second biometric signal in the secondary monitoring device 130 where both the first and second biometric signals are descriptive of the same biometric characteristic of the human subject, in other examples either the primary monitoring device 110, the secondary monitoring device 130 or both may be capable of deriving one or more respective further biometric signals.

In an example, the secondary monitoring device 130 may be capable of deriving one or more further biometric signals that are descriptive of the respective one or more further biometric characteristics (that are different from the biometric characteristics represented by the second biometric signal) in addition to the second biometric signal and provide information carried therein via the wireless link 102 upon request. In such a scenario, the device control signaling exemplified by the step 308 of FIG. 5 may further comprise a request for the secondary monitoring device 130 to provide biometric information (e.g. the respective sequence of sample values) pertaining to the biometric signal that pertains to a biometric characteristic identified in the request.

In another example, the primary monitoring device 110 may be capable of deriving one or more further biometric signals that are descriptive of the respective one or more further biometric characteristics (that are different from the biometric characteristics represented by the first biometric signal) in addition to the first biometric signal. In such a scenario, the operation in the primary monitoring device 110 may involve disabling derivation of one or more of the further biometric signals together with disabling the derivation of the first biometric signal in response to the secondary biometric information received from the secondary monitoring device 130 suggesting a normal condition of the human subject in view of the certain biometric characteristics (that is presented by the first biometric signal and the secondary biometric information).

In the foregoing, an implicit assumption is that the first biometric signal derived in the primary monitoring device 110 and the second biometric signal derived in the secondary monitoring device 130 are descriptive of the same biometric characteristic of the human subject. In another example, the first biometric signal derived in the primary monitoring device 110 is descriptive of a first biometric characteristic and the second biometric signal derived in the secondary monitoring device 130 is descriptive of a second biometric characteristic that is different the first biometric characteristic (in other words, the second biometric signal in not descriptive of the same biometric characteristic as the first biometric signal). In such a scenario, there is a predefined relationship between the first and second biometric characteristics, which can be assumed to make the first biometric signal redundant or substantially redundant when the secondary biometric information is available. Non-limiting examples of such relationship between the first and second biometric characteristics include the following:

- The first biometric characteristic may be derivable from the second biometric characteristic, e.g. such that one or more sample values of the first biometric characteristic may be derivable from or in dependence of one or more sample values of the second biometric characteristic. The derivation may be carried out e.g. by using a predefined derivation rule, formula or algorithm. A non-limiting example in this regard involves the first biometric characteristic that comprises heart rate and the second biometric characteristic that comprises ECG, where a biometric signal descriptive of the heart rate is derivable on basis of the peaks identifiable in the biometric signal descriptive of the ECG.
- The second biometric characteristic may serve, at least in part, as an indication of the same physical phenomenon as the first biometric characteristic, and hence determination that the secondary biometric information suggests (e.g. according to the one or more predefined criteria described in the foregoing) a normal condition or an abnormal condition of the human subject implies that similar outcome would also be derivable on basis of the primary biometric information. A non-limiting example in this regard involves the first biometric characteristic that comprises blood pressure and the second biometric characteristic that comprises pulse transmit time (PTT), which are a pair of biometric characteristics that both can be applied in monitoring of blood pressure of the human subject and that have a known relationship between each other.

Referring back to components of the primary monitoring device 110 and the secondary monitoring device 130 depicted in FIGS. 2 and 3, respectively, the processor 116, 136 is configured to read from and write to the respective memory 115, 135. Although each of the processors 116, 136 is depicted as a respective single component, any of the processors 116, 136 may be implemented as respective one or more separate processing components. Similarly, although each of the memories 115, 135 is depicted as a respective single component, any of the memories 115, 135 may be implemented as respective one or more separate components, some or all of which may be integrated/removable and/or may provide permanent/semi-permanent/dynamic/cached storage.

The memory 115, 135, may store the respective computer program 117, 137 comprising computer-executable instructions that control the operation of the respective monitoring device 110, 130 when loaded into the respective processor 116, 136. As an example, the computer program 117 may include one or more sequences of one or more instructions. The computer program 117 may be provided as a computer program code. The processor 116 is able to load and execute the computer program 117 by reading the one or more sequences of one or more instructions included therein from the memory 115. The one or more sequences of one or more instructions may be configured to, when executed by the processor 116, cause the primary monitoring device 110 to carry out operations, procedures and/or functions described in the foregoing. Hence, the primary monitoring device 110 may comprise at least one processor 116 and at least one memory 115 including computer program code for one or more programs, the at least one memory 115 and the computer program code configured to, with the at least one processor 116, cause the primary monitoring device 110 to perform operations, procedures and/or functions described in the foregoing. Similar considerations are equally valid for corresponding components 13x of the secondary monitoring device 130.

Each of the computer programs 117, 137 may be provided e.g. as a respective computer program product comprising at least one computer-readable non-transitory medium having program code stored thereon, the program code, when executed by the respective monitoring device 110, 130, causes the monitoring device 110, 130 at least to perform operations, procedures and/or functions described in the foregoing in context of the respective monitoring device 110, 130. The computer-readable non-transitory medium may comprise a memory device or a record medium such as a CD-ROM, a DVD, a Blu-ray disc or another article of manufacture that tangibly embodies the computer program. As another example, the computer program may be provided as a signal configured to reliably transfer the computer program.

Reference(s) to a processor should not be understood to encompass only programmable processors, but also dedicated circuits such as field-programmable gate arrays (FPGA), application specific circuits (ASIC), signal processors, etc. Features described in the preceding description may be used in combinations other than the combinations explicitly described.

Although functions have been described with reference to certain features, those functions may be performable by other features whether described or not. Although features have been described with reference to certain embodiments, those features may also be present in other embodiments whether described or not.

The invention claimed is:

1. A method, comprising:
   deriving, by a device, on basis of one or more sensor signals that are descriptive of respective characteristics of a body of a living subject, at least a first biometric signal that is descriptive of a first biometric characteristic of said subject;
   detecting, by the device, a presence of another device that is capable of providing, over a wireless link, information carried in a second biometric signal that is descriptive of a second biometric characteristic of a subject;
   receiving, by the device, from the detected device via the wireless link, one or more values of the second biometric characteristic carried in said second biometric signal; and
   selectively disabling, by the device, derivation of said first biometric signal in dependence of said one or more values of the second biometric characteristic received from said detected device, wherein the first biometric signal is selectively disabled while the one or more values of the second biometric characteristic are indicating a normal condition of said subject.

2. The method according to claim 1 wherein said detecting presence of another device comprises detecting presence of said another device in response to detecting that said another device is in close proximity to the device.

3. The method according to claim 2, wherein detecting that said another device is in close proximity to the device comprises one of:
   deriving a received signal strength indication, RSSI, that is descriptive of the signal strength of one or more device discovery messages received from said another device via the wireless link; and
   detecting that the derived RSSI exceeds a predefined threshold value.

4. The method according to claim 1, wherein said detecting presence of another device comprises
   carrying out a device discovery procedure to detect presence of another device;
   carrying out a service discovery procedure to detect availability of information descriptive of the second biometric characteristic in the detected another device; and
   verifying that the information descriptive of the second biometric characteristic in the detected another device is descriptive of the second biometric characteristic of the same subject.

5. The method according to claim 4, wherein the second biometric characteristic is the same as the first biometric characteristic and wherein said verifying comprises
   receiving, from the detected another device, one or more values of the second biometric characteristic;
   verifying that the difference between one or more values of the second biometric characteristic received from the detected another device to temporally corresponding values of the first biometric characteristics carried in the first biometric signal derived in the device is smaller than a predefined margin.

6. The method according to claim 1, wherein the first biometric signal is one of enabled or re-enabled when the one or more values of the second biometric characteristic indicate an abnormal condition of the subject.

7. The method according to claim 6, wherein said transmitting comprises transmitting one or more values of the first biometric characteristic in response to one or more values of the second biometric characteristic received from said detected device or a value derived therefrom failing to meet predefined criteria.

8. The method according to claim 6, wherein said transmitting comprises relaying one or more values of the second biometric characteristic received from said detected device in response to these values or a value derived therefrom meeting predefined criteria.

9. The method according to claim 1, further comprising, controlling provision of the values of the second biometric characteristic from the detected device, including one or more of the following:
   requesting the detected device to provide the values of the second biometric characteristic at a desired accuracy,
   requesting the detected device to provide the values of the second biometric characteristic at an indicated sampling rate,
   requesting the detected device to transmit the values of the second biometric characteristic in a sequence of messages that are transmitted from the detected device at an indicated rate,
   requesting the detected device to transmit the values of the second biometric characteristic in a sequence of messages such that each message includes an indicated number of consecutive values of the first biometric characteristic.

10. The method according to claim 1, wherein the second biometric characteristic is the same as the first biometric characteristic.

11. A device comprising
   a sensor portion deriving, on basis of one or more sensor signals that are descriptive of respective characteristics of a body of a living subject, at least a first biometric signal that is descriptive of a first biometric characteristic of said subject;
   a communication apparatus performing wireless communication over a wireless link; and
   a control portion arranged to cause the device to perform at least the following:
   detect presence of another device that is capable of providing, over the wireless link, information carried in a second biometric signal that is descriptive of a second biometric characteristic of the same subject,
   receive, from the detected device via the wireless link, one or more values of the second biometric characteristic carried in said second biometric signal, and
   selectively disable derivation of said first biometric signal in dependence of said one or more values of the second biometric characteristic received from said detected device, wherein the first biometric signal is selectively disabled while the one or more values of the second biometric characteristic are indicating a normal condition of said subject.

12. The device according to claim 11, wherein the sensor portion comprises one or more sensors capturing said one of or more sensor signals and an analysis portion deriving said first biometric signal on basis of said one or more sensor signals,
   wherein disabling derivation of said first biometric signal comprises disabling operation of the analysis portion with respect to derivation of the first biometric signal.

13. The device according to claim 12, wherein disabling derivation of said first biometric signal comprises further disabling operation the sensor portion with respect to employing said one or more sensors capturing said one or more sensor signals.

14. The device according to claim 11 wherein said detecting presence of another device comprises detecting presence of said another device in response to detecting that said another device is in close proximity to the device.

15. The device according to claim 14, wherein detecting that said another device is in close proximity to the device comprises
   deriving a received signal strength indication, RSSI, that is descriptive of the signal strength of one or more device discovery messages received from said another device via the wireless link; and
   detecting that the derived RSSI exceeds a predefined threshold value.

16. The device according to claim 11, wherein said detecting presence of another device comprises
   carrying out a device discovery procedure to detect presence of another device;
   carrying out a service discovery procedure to detect availability of information descriptive of the second biometric characteristic in the detected another device; and
   verifying that the information descriptive of the second biometric characteristic in the detected another device is descriptive of the second biometric characteristic of the same subject.

17. The device according to claim 16, wherein the second biometric characteristic is the same as the first biometric characteristic and wherein said verifying comprises
   receiving, from the detected another device, one or more values of the second biometric characteristic;
   verifying that the difference between one or more values of the second biometric characteristic received from the detected another device to temporally corresponding values of the first biometric characteristics carried in the first biometric signal derived in the device is smaller than a predefined margin.

18. The device according to claim 11, further comprising transmitting one or more values of the first biometric characteristic in response to one or more values of the second biometric characteristic received from said detected device or a value derived therefrom failing to meet predefined criteria.

19. The device according to claim 18, wherein said transmitting comprises relaying one or more values of the second biometric characteristic received from said detected device in response to these values or a value derived therefrom meeting predefined criteria.

20. The device according to claim 11, wherein the control portion further causes the device to control provision of the values of the second biometric characteristic from the detected device, including one or more of the following:
   requesting the detected device to provide the values of the second biometric characteristic at a desired accuracy,
   requesting the detected device to provide the values of the second biometric characteristic at an indicated sampling rate,
   requesting the detected device to transmit the values of the second biometric characteristic in a sequence of messages that are transmitted from the detected device at an indicated rate,
   requesting the detected device to transmit the values of the second biometric characteristic in a sequence of messages such that each message includes an indicated number of consecutive values of the first biometric characteristic.

* * * * *